US010238761B1

(12) United States Patent
Adiga et al.

(10) Patent No.: US 10,238,761 B1
(45) Date of Patent: Mar. 26, 2019

(54) METHOD AND AN INTEGRATED DEVICE FOR AN AREA DECONTAMINATION PROCESS

(71) Applicant: NANOMIST SYSTEMS, LLC, Macon, GA (US)

(72) Inventors: Kayyani C. Adiga, Macon, GA (US); Rajani Adiga, Macon, GA (US); Robert F. Hatcher, Jr., Macon, GA (US)

(73) Assignee: Nanomist Systems, LLC, Macon, GA (US)

( * ) Notice: Subject to any disclaimer, the term of this patent is extended or adjusted under 35 U.S.C. 154(b) by 1 day.

(21) Appl. No.: 15/233,581

(22) Filed: Aug. 10, 2016

Related U.S. Application Data

(63) Continuation-in-part of application No. 13/963,967, filed on Aug. 9, 2013.

(51) Int. Cl.

| | |
|---|---|
| ***A61L 2/22*** | (2006.01) |
| ***A61L 9/14*** | (2006.01) |
| ***A61L 2/20*** | (2006.01) |
| ***A61L 9/04*** | (2006.01) |
| ***A61L 9/12*** | (2006.01) |
| ***A61L 2/24*** | (2006.01) |

(52) U.S. Cl.
CPC *A61L 2/22* (2013.01); *A61L 2/20* (2013.01); *A61L 2/202* (2013.01); *A61L 2/204* (2013.01); *A61L 2/208* (2013.01); *A61L 2/24* (2013.01); *A61L 9/04* (2013.01); *A61L 9/12* (2013.01); *A61L 9/14* (2013.01); *A61L 2202/14* (2013.01); *A61L 2202/15* (2013.01); *A61L 2202/25* (2013.01); *A61L 2209/111* (2013.01); *A61L 2209/13* (2013.01); *A61L 2209/135* (2013.01); *A61L 2209/211* (2013.01); *A61L 2209/212* (2013.01)

(58) Field of Classification Search
CPC .................................. A61L 2/22; A61L 2/208
USPC ........................................................... 422/28
See application file for complete search history.

(56) References Cited

U.S. PATENT DOCUMENTS

| | | | |
|---|---|---|---|
| 7,326,382 B2 | 2/2008 | Adiga et al. | |
| 7,354,551 B2 | 4/2008 | Mielnik et al. | |
| 7,604,774 B2 | 10/2009 | Mole et al. | |
| 8,889,081 B2 | 11/2014 | Schwartz et al. | |
| 9,011,787 B2 | 4/2015 | Dunkley et al. | |
| 9,050,481 B2 | 6/2015 | Fenton et al. | |
| 9,072,804 B2 | 7/2015 | Dunkley et al. | |
| 9,186,428 B2 | 11/2015 | Jennings | |
| 9,375,500 B2 | 6/2016 | Dunkley et al. | |
| 2003/0031589 A1 | 2/2003 | Martin et al. | |
| 2006/0008378 A1 | 1/2006 | Imai et al. | |
| 2008/0267818 A1 | 10/2008 | Hill | |
| 2013/0302207 A1* | 11/2013 | Ahiska | A61L 2/208 422/3 |

OTHER PUBLICATIONS

Portner et al., Sporicidal effect of peracetic acid vapor, 1968, Applied Microbiology, vol. 16 No. 11, pp. 1782-1785 (Year: 1968).*
Barbut et al. Activity in vitro of hydrogen peroxide vapour against Clostridium difficile spores, Nov. 17, 2011, Journal of Hospital Infection, pp. 88-87.
International Agency for Research on Cancer, IARC Monographs on the evaluation of carcinogenic risks to humans, 1999, p. 671.
Johnston et al., Evaluation of hydrogen peroxide vapour as a method for the decontamination of surfaces contaminated with Clostridium botulinum spores, 2005, Journal of Microbiological Methods, 60, pp. 403-411.
Pottage et al., Low-Temperature Decontamination with Hydrogen Peroxide or Chlorine Dioxide for Space Applications, Jun. 2012, Applied and Environmental Microbiology, 78 (12), pp. 4169-4174.

* cited by examiner

*Primary Examiner* — Kevin Joyner
*Assistant Examiner* — Holly M Mull
(74) *Attorney, Agent, or Firm* — Law Office of J. L. Simunic; Joan L. Simunic

(57) ABSTRACT

The present invention is an improved method for decontamination of a space and an integrated device that completes the decontamination cycle extremely fast while still being compact, lightweight, simple to operate and easy to move as a single unit. The method of the present invention delivers less biocide than is used in prior art methods at a very high rate of flux, allows the biocide to reside in the space being decontaminated to achieve a predetermined kill level, and then aerates the space. Because a nominal amount of biocide is used, there is less biocide to remove from the space than in prior art methods thereby reducing the time required for aeration and shortening the downtime for safe entry of the facility.

7 Claims, No Drawings

METHOD AND AN INTEGRATED DEVICE FOR AN AREA DECONTAMINATION PROCESS

CROSS-REFERENCE TO PRIOR APPLICATIONS

The present application claims priority to U.S. patent application Ser. No. 13/963,967, filed Aug. 9, 2013, currently pending, which is incorporated herein in its entirety by reference.

BACKGROUND

The present development is an improved method and an integrated device that provides a fast method for the decontamination or inactivation of biological contaminants or microorganisms using a biocide or biocidal agents, and the subsequent aeration of an area. The decontamination process is highly effective because the rapid injection of the biocide into the area or volume causes a sudden shock to the biological contaminants reducing the concentration of biocide necessary for an effective kill of the contaminant. Because there is less biocide present in the area than the amount required according to the prior art, the time required to remove the residual biocide from the area, or the aeration time, is reduced. Thus, the faster biocide injection time combined with the shorter aeration time results in an overall decontamination cycle is shortened relative to the prior art methods.

The method and device of the present application may be used for rapid decontamination of enclosed areas such as hotel rooms, hospitals, airports, cruise ships, clean rooms, laboratories, and many public and private facilities. With the continuing spread of resistant bacterial and viral pathogens, such as MRSA (methicillin-resistant *staphylococcus aureus*), c.diff (*clostridium difficile*), rotavirus, rhinovirus, and other pathogens such as stachybotrys mold, there is a growing need for an effective, economical, and rapid method of decontamination. As is known in the art, a variety of biocides may be used for decontamination depending on the targeted pathogen or pathogens. Some commonly used biocides are hydrogen peroxide, formaldehyde, alcohol, peracetic acid, and ozone.

In a typical decontamination process a mist or vapor of aqueous hydrogen peroxide (HP) floods the area to be decontaminated or sterilized, with the HP concentrations being allowed to reach levels of 2000 ppm or more. Following decontamination, the enclosed area must be aerated to reduce the HP concentration to a safe level, normally defined as less than about 1 ppm. A typical decontamination time for a 36 $m^3$ room is from about one to about four hours.

In the prior art, the decontamination system normally comprises at least a biocide vapor production and delivery module and a separate aeration module. Although functional, multiple unit systems are not easy to transport and operate, and scalability, weight, cost and overhead can be a concern. Thus, there is a need for an integrated decontamination device which synthesizes all functions in one device that is compact, lightweight, and portable. Further, the total cycle time, i.e. the introduction of the biocide, residence time for biocide to function, and aeration of the decontaminated space, should be as short as possible in order to maximum the potential utilization of the space.

SUMMARY OF THE PRESENT INVENTION

The present invention is an improved method for decontamination of a space and an integrated device that completes the decontamination cycle extremely fast while still being compact, lightweight, simple to operate and easy to move as a single unit. The method relies on three factors: (1) the rapid delivery of biocide shocks a target pathogen, (2) once shocked, the pathogen succumbs to a lower concentration of biocide than if the pathogen is slowly exposed to the biocide, and (3) by using a lower concentration of biocide to effect a kill of the pathogen less time is required for aeration to return to space to a safe biocide exposure limit level. Specifically, the method of the present invention delivers less biocide than is used in prior art methods at a very high rate of flux, allows the biocide to reside in the space being decontaminated to achieve a predetermined kill level, and then aerates the space. Because a nominal amount of biocide is used, there is less biocide to remove from the space than in prior art methods thereby reducing the time required for aeration and shortening the downtime for safe entry of the facility.

The area decontamination apparatus made according to the present invention comprises at least one optional preconditioning module; a decontamination module; an aeration module; a sensor array to monitor temperature, biocide vapor detection, and relative humidity; and a decontamination cycle controller. The system is designed to allow the biocide to be injected into the area or volume at an extremely high rate, such that the peak concentration of biocide is reached very rapidly. The use of a honeycomb catalyst in the aerator module has been found to be highly effective. Optionally, the system is automated and may include sensors for environmental relative humidity (RH %), temperature, biocide low concentration range (HP-LC) and biocide high concentration (HP-HC).

DETAILED DESCRIPTION OF THE INVENTION

The following description is intended to provide the reader with a better understanding of the invention. The description is not intended to be limiting with respect to any element not otherwise limited within the claims.

The present invention discloses a method for rapidly decontaminating areas, both large and small, and a device for practicing the method. The area can comprise single, double or multiple rooms. The room might have a variety of furnishings, such as wall-to-wall carpet, hardwood floors, fabric or other soft surfaces, porcelain and/or marble surfaces, or other materials commonly found in hotels rooms or bathrooms.

The method comprises a three step process: (1) rapid delivery of a biocide into a predetermined area to shock the target pathogen, wherein the amount of biocide delivered is approximately equal to the minimum concentration required to kill the pathogen, (2) allowing the biocide to remain in contact with the pathogen for a period of time necessary to effect at least a 4-log kill, but for no longer than 25 minutes, and (3) removing residual or unreacted biocide from the area to a safe biocide exposure limit level. As used herein, the term "biocide" is refers to a single chemical agent or a combination of chemical agents that are used for sanitation and decontamination purposes.

The method is preferably carried out using a device comprising two modules: 1) a decontamination module that produces and disperses biocide vapor into the area, and 2) an aeration module that removes residual biocide. In a preferred embodiment, the decontamination module and the aeration module are automated and operated by a control system. Optionally, a module may be included which is used to control humidity for conditioning the room to a predetermined initial relative humidity or % RH.

The primary function of the decontamination module is to deliver biocide throughout the area to inactivate or kill any microorganisms present in the area. In an exemplary embodiment, the decontamination or biocide discharging module comprises a liquid handling system, an ultrafine mist production unit, and the premix evaporator with a heating source that work in series to produce a condensed biocide vapor cloud. The ultrafine mist production unit and premix evaporation device are described more fully in U.S. Pat. Nos. 6,883,724 and 7,744,786 and 7,524,442, and in pending patent application U.S. Ser. No. 13/945,897, all of which are incorporated herein in their entireties by reference. After exiting the decontamination module, the cloud disperses as condensed vapor throughout the area or room, the characteristics of the vapor depending on the temperature, RH, and mixing and turbulence. The rate of production of the vapor will depend on the mist rate. It is preferable that the premix evaporator can produce condensed vapor of 35% hydrogen peroxide at a rate of up to 50-60 g/min using a single power line with about 1800 Watts. The biocide vapor may traverse through open doorways into multiple rooms, as encountered in hotels, office buildings, or other common structures.

The primary function of the aeration module is to remove residual biocide from the area after any microorganisms have been killed by the biocide. In an exemplary embodiment, the aerator module comprises catalyst panels for decomposing biocide vapors. For example, if the biocide is hydrogen peroxide, contact with the catalyst panels results in decomposition to $H_2O$ and 02. Cleaned air exits from the catalyst panels and is circulated back into the area. The typical aeration rates vary from 1-4 g/min depending on the injected biocide mass, the rate of its injection, and the duration of its hold time in the room. As is known in the art, aeration ideally continues until the concentration of biocide drops to 1.0 ppm or less.

Returning to the method for decontamination, the first step is the rapid delivery of the biocide into a predetermined area to shock the target pathogen, wherein the amount of biocide delivered is approximately equal to the minimum concentration required to kill the pathogen at the desired efficiency level. A number of biocides are known in the art and any may be used in the present method, either alone or in combination. Some commonly used biocides are hydrogen peroxide, formaldehyde, alcohol, peracetic acid, ozone, and a combination thereof. As is known in the art, the kill process or inactivation efficiency is expressed in terms "log kill". For example, 4-log kill refers to sanitation, 5-log kill refers to disinfection, and; 6-log kill refers to a complete sterilization condition.

As is known in the art, the amount of biocide to be delivered, or target mass concentration, is determined based on the room size, the target pathogen, the room environmental conditions and level of disinfection desired, as is known in the art. The target mass concentration is expressed in terms of grams per cubic meter ($g/m^3$) and is calculated from the mass delivered and the room volume. In a preferred embodiment, the amount of biocide used is equal to not more than about 130% of the minimum concentration level required to kill the pathogen. As a general guideline, it is recommended that for a 4-log kill a minimum concentration of 0.6+/−0.2 $g/m^3$ biocide be used, and for a 5-log kill a minimum concentration of 0.7+/−0.2 $g/m^3$ biocide be used, and for a 6-log kill a minimum concentration of 1.7+/−0.2 $g/m^3$ biocide be used in the present method.

In order to effect the desired log kill using a minimum amount of biocide, the target mass concentration must be delivered at a rapid rate relative to the teachings of the prior art. Specifically, the biocide must be delivered into the area at a rate of at least 0.1 g biocide per cubic meter of area per minute. In a more preferred embodiment, the biocide is delivered into the area at a rate of at least 0.2 g biocide per cubic meter of area per minute. In a most preferred embodiment, the biocide is delivered into the area at a rate of at least 0.3 g biocide per cubic meter of area per minute.

The second step of the present method requires allowing the biocide to remain in contact with the pathogen for a period of time necessary to effect at least a 4-log kill, but for no longer than 25 minutes, referred to herein as the "biocide residence time". The biocide residence time is the period during which the biocide is present within the area and can have contact with the pathogen to effect the kill. The biocide residence time is calculated from the beginning of the biocide injection process until the aeration process is initiated. Because the pathogens are effectively shocked by the rapid injection of biocide in the first step of the present method, the time required to kill a sufficient concentration to reach the desired log kill level is shorter than the methods of the prior art and effective kills are obtained in periods of not more than 25 minutes.

The third step of the present method requires removing residual or unreacted biocide from the area to a safe biocide exposure limit level. Preferably the biocide concentration level should be not greater than about 1 ppm in the area following aeration. Aeration methods are well known in the art and any aeration method may be used in the third step of the present invention. It is recommended, however, to use a high efficiency aeration device.

The following presents representative data and are representative examples using the method and the decontamination and aeration device of the present development. These examples are presented to further explain the invention and are not intended, or to be taken, to limit the scope of the invention.

Tests were conducted in a 36 $m^3$ room without carpet (i.e., with tiled floor) and also in a 110 $m^3$ room with wall-to-wall carpet and configured to simulate a larger room with an attached bathroom with a door opening. Biological indicator (BI) test disks inoculated with 4-log, 5-log and 6-log populations of G. *Stearothermophilus* prepared by Mesa Labs were used.

BI test disks were placed at various locations within the room and doors and windows and other ventilation to the room was closed. Room temperature was not intentionally controlled, but was maintained at between about 22° C. and 26° C. The test area was pre-conditioned to a relative humidity of about 50%. A predetermined amount of biocide, a 35% hydrogen peroxide vapor, was rapidly injected into the room, with the rate of injection being about 50 g per minute or producing about 17.5 g of HP vapor per minute. The "inactivation time" or time from the initiation of the biocide injection through the residence time was a total of about 10 minutes. The room was then aerated until the concentration of biocide dropped to about 1 ppm. The overall cycle time was then calculated as the time for biocide injection, biocide contact or inactivation time, and the aeration time.

Table I shows the kill efficiency for different mass concentrations of 35% HP solution injected into a 36 $m^3$ room at a rate of from 2.4 g/min to 17.4 g/min. As indicated, using the method of the present invention significantly improves the efficiency of the decontamination process because by using a fast biocide injection essentially the same amount of biocide can accomplish a 10-fold greater kill level (6-log versus 5-log) while simultaneously reducing the biocide injection time by approximately 35%.

TABLE 1

| Test # | Injected mass ($g/m^3$) | Mass of 35% HP solution (g) | HP mass injected (g) | Injection time (min) | Injection rate (g/min) of HP | Injection rate (g/min/ m3) of HP | Kill Efficiency |
|---|---|---|---|---|---|---|---|
| 1 | 2.4 | 247 | 86.4 | 30 | 2.9 | 0.08 | |
| 2 | 2.4 | 247 | 86.4 | 20 | 4.3 | 0.12 | |
| 3 | 2.4 | 247 | 86.4 | 12.7 | 6.8 | 0.19 | 5-log |
| 4 | 2.4 | 247 | 86.4 | 8.3 | 10.4 | 0.29 | 6-log |
| 5 | 2 | 206 | 72 | 30 | 2.4 | 0.07 | |
| 6 | 2 | 206 | 72 | 20 | 3.6 | 0.10 | |
| 7 | 2 | 206 | 72 | 12 | 6.0 | 0.17 | 5-log |
| 8 | 2 | 206 | 72 | 6.5 | 11.1 | 0.31 | 6-log |
| 9 | 2 | 208 | 72.7 | 9.6 | 7.6 | 0.21 | 5-log |
| 10 | 2 | 209 | 73.1 | 6.5 | 11.2 | 0.31 | 6-log |
| 11 | 2.2 | 227 | 79.6 | 13 | 6.1 | 0.17 | 5-log |
| 12 | 2.1 | 214 | 74.9 | 4.3 | 17.4 | 0.48 | 6-log |

In a typical decontamination process a mist or vapor of aqueous hydrogen peroxide floods the area to be decontaminated or sterilized, the biocide is allowed to reside in the area for a predetermined period of time, and then the enclosed area must be aerated to reduce the HP concentration. A typical decontamination time for a 36 $m^3$ room is from about one hour to about four hours. Table 2 shows the total cycle time for achieving a 4-log kill, a 5-log kill and a 6-log kill in a 36 $m^3$ room using the method and apparatus of the present invention. In other words, assuming that the highest efficiency prior art method can achieve 6-log decontamination in about one hour, the method of the present invention can achieve the 6-log kill in less than 75% of the time required for the prior art methods in a 36 $m^3$ room and can achieve a 6-log kill in a 100 $m^3$ room in about the same amount of the time required for the prior art methods to decontaminate a 36 $m^3$ room.

TABLE 2

| Test # | A | B | C | D | E |
|---|---|---|---|---|---|
| Room Size | 36-$m^3$ | 36-$m^3$ | 36-$m^3$ | 100-$m^3$ | 100-$m^3$ |
| Floor covering | tile | tile | tile | carpet[A] | carpet[A] |
| Injected mass ($g/m^3$) | 0.6 | 0.7 | 1.7 | 0.8 | 1.8 |
| Mass of 35% HP solution (g) | 62 | 74 | 168 | 260 | 573 |
| HP mass injected (g) | 22 | 26 | 59 | 91 | 201 |
| Injection rate (g/min) of HP | 11.4 | 11.0 | 12.3 | 13.0 | 21.1 |
| Injection time (min) | 1.8 | 2.4 | 4.8 | 7.0 | 9.5 |
| Residence time (min) | 8.2 | 7.6 | 5.2 | 3.0 | 0.5 |
| Aeration time (min) | 15 | 18 | 35 | 40 | 51 |
| Total cycle time (min) | 25 | 28 | 45 | 50 | 61 |
| Kill Efficiency | 4-log | 5-log | 6-log | 5-log | 6-log |

[A]Room included a second doorway and placed a BI sample non-line of sight through the doorway.

The relatively short kill time of the present invention additionally provides a secondary benefit. Because the biocide has a shorter residence time than the prior art methods, absorption of biocide by room surfaces and contents of the room is reduced.

As shown, the present invention is an improved method for decontamination of a space. The method relies on three factors: (1) the rapid delivery of biocide shocks a target pathogen, (2) once shocked, the pathogen succumbs to a lower concentration of biocide than if the pathogen is slowly exposed to the biocide, and (3) by using a lower concentration of biocide to effect a kill of the pathogen less time is required for aeration to return to space to a safe biocide exposure limit level. An integrated device that completes the decontamination cycle extremely fast while still being compact, lightweight, simple to operate and easy to move as a single unit is recommended.

Unless defined otherwise, all technical and scientific terms used herein have the same meaning as commonly understood by one of ordinary skill in the art to which the presently disclosed subject matter pertains. Representative methods, devices, and materials are described herein, but are not intended to be limiting unless so noted.

The terms "a", "an", and "the" refer to "one or more" when used in the subject specification, including the claims. Thus, for example, reference to "a pathogen" includes a plurality of such pathogens, and so forth.

Unless otherwise indicated, all numbers expressing quantities of components, conditions, and otherwise used in the specification and claims are to be understood as being modified in all instances by the term "about". Accordingly, unless indicated to the contrary, the numerical parameters set forth in the instant specification and attached claims are approximations that can vary depending upon the desired properties sought to be obtained by the presently disclosed subject matter.

As used herein, the term "about", when referring to a value or to an amount of mass, weight, time, volume, concentration, or percentage can encompass variations of, in some embodiments ±20%, in some embodiments ±10%, in some embodiments ±5%, in some embodiments ±1%, in some embodiments ±0.5%, and in some embodiments to ±0.1%, from the specified amount, as such variations are appropriate in the disclosed application.

Specific dimensions and process details relevant to the decontamination device are provided herein for the purpose of demonstrating the invention, but these dimensions are not intended to limit the scope of the invention and those who are skilled in the art may make various other changes and modifications without departing from the true spirit and scope of present invention. We intend to cover all such changes in our claims listed below which are within the scope of current disclosure.

What is claimed is:

1. A method of decontaminating a space with a biocide comprising the steps of:

a. providing a biocide effective for killing a pathogen, wherein said biocide is hydrogen peroxide and wherein said biocide is provided in the form of a mist, a vapor or a condensed vapor, wherein the amount of said biocide delivered into the space is not more than 30% greater than the minimum concentration required to kill the pathogen and not greater than 2.46 $g/m^3$ and wherein said biocide is delivered into the space at a rate of at least 0.1 $g/min/m^3$;

b. allowing said biocide to reside in the space for a residence time sufficient to effect at least a 4-log kill, but not longer than 15 minutes; and, c. reducing said biocide to a level of not more than 1.0 ppm by using an aeration process, and wherein the residence time is defined as the difference between time the biocide begins to be introduced into the space and the time the aeration process is initiated.

2. The method of claim 1 wherein said biocide is delivered at a rate of at least 0.2 $g/min/m^3$.

3. The method of claim 1 wherein said biocide is delivered at a rate of at least 0.3 g/min/$m^3$.

4. The method of claim 1 wherein said biocide residence time is sufficient to effect at least a 5-log kill but not longer than 20 minutes.

5. The method of claim 1 wherein said biocide residence time is sufficient to effect at least a 6-log kill but not longer than 25 minutes.

6. The method of claim 1 wherein the space defines a volume and said volume is preconditioned to a relative humidity of less than 60% prior to presentation of said biocide.

7. The method of claim 1 wherein the biocide injection is terminated based upon delivering a predetermined target level of biocide vapor into the space.

* * * * *